United States Patent
Mirza et al.

(10) Patent No.: US 10,092,243 B2
(45) Date of Patent: Oct. 9, 2018

(54) PED—ENDOSCOPE IMAGE AND DIAGNOSIS CAPTURE SYSTEM

(71) Applicant: THE TRUSTEES OF THE UNIVERSITY OF PENNSYLVANIA, Philadelphia, PA (US)

(72) Inventors: Natasha Mirza, Bryn Mawr, PA (US); Jason Brant, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 302 days.

(21) Appl. No.: 14/061,186

(22) Filed: Oct. 23, 2013

(65) Prior Publication Data
US 2014/0051923 A1 Feb. 20, 2014

Related U.S. Application Data

(63) Continuation of application No. PCT/US2012/036573, filed on May 4, 2012.
(Continued)

(51) Int. Cl.
| | |
|---|---|
| *A61B 1/00* | (2006.01) |
| *A61B 1/04* | (2006.01) |
| *A61B 1/06* | (2006.01) |
| *A61B 5/00* | (2006.01) |
| *G06F 1/16* | (2006.01) |

(52) U.S. Cl.
CPC ........ *A61B 5/6898* (2013.01); *A61B 1/00009* (2013.01); *A61B 1/00022* (2013.01); *A61B 1/00041* (2013.01); *A61B 1/00052* (2013.01); *A61B 1/00126* (2013.01); *A61B 1/00195* (2013.01); *A61B 1/04* (2013.01);
(Continued)

(58) Field of Classification Search
CPC ............ A61B 1/00009; A61B 1/00022; A61B 1/00041; A61B 1/00052; A61B 1/00126; A61B 1/00195; A61B 1/04; A61B 1/042; G06F 1/1626; G06F 1/1686
USPC ....... 600/103, 109, 112, 160, 162, 168, 175, 600/176; 348/65; 359/642
See application file for complete search history.

(56) References Cited

U.S. PATENT DOCUMENTS

2002/0107530 A1* 8/2002 Sauer .................. A61B 1/0014
606/139
2007/0258150 A1* 11/2007 Takato ............... G02B 13/0045
359/686

(Continued)

*Primary Examiner* — John P Leubecker
*Assistant Examiner* — William Chou
(74) *Attorney, Agent, or Firm* — Baker Botts, LLP

(57) ABSTRACT

A personal electronic device (PED)-endoscope image and diagnosis capture system is provided. The system includes a PED adapter having a magnification lens connection side and a PED connection side. A magnification lens is connectable with the lens connection side of the PED adapter. An eyepiece lens coupler is also provided and connects the magnification lens to the endoscope eyepiece. A PED is connected to the PED adapter and includes a processor, a memory and an image capture system with a PED lens. The PED adapter aligns the magnification lens with the PED lens. The processor is configured to activate the image capture system using a remote or voice-activated trigger signal and store captured images in the PED memory. Patient data and examination data can be associated with the images, and the images and data can be transferred from the PED to an electronic medical records system.

16 Claims, 7 Drawing Sheets

Related U.S. Application Data

(60) Provisional application No. 61/483,302, filed on May 6, 2011.

(52) U.S. Cl.
CPC ............ *A61B 1/042* (2013.01); *G06F 1/1626* (2013.01); *G06F 1/1686* (2013.01); *G06F 2200/1633* (2013.01)

(56) References Cited

U.S. PATENT DOCUMENTS

| | | |
|---|---|---|
| 2007/0280677 A1 | 12/2007 | Drake et al. |
| 2008/0198223 A1 | 8/2008 | Iriyama et al. |
| 2008/0207996 A1* | 8/2008 | Tsai ................... A61B 1/00048 600/112 |
| 2008/0303899 A1 | 12/2008 | Berci et al. |
| 2009/0080088 A1* | 3/2009 | Ohashi ................. G02B 15/173 359/687 |
| 2010/0053770 A1* | 3/2010 | Sato ................... G02B 13/0085 359/717 |
| 2010/0145146 A1 | 6/2010 | Molder et al. |
| 2011/0263983 A1* | 10/2011 | Peszynski ............ A61B 1/0052 600/443 |
| 2012/0010670 A1* | 1/2012 | Pisarnwongs ...... A61B 17/3421 606/86 R |

* cited by examiner

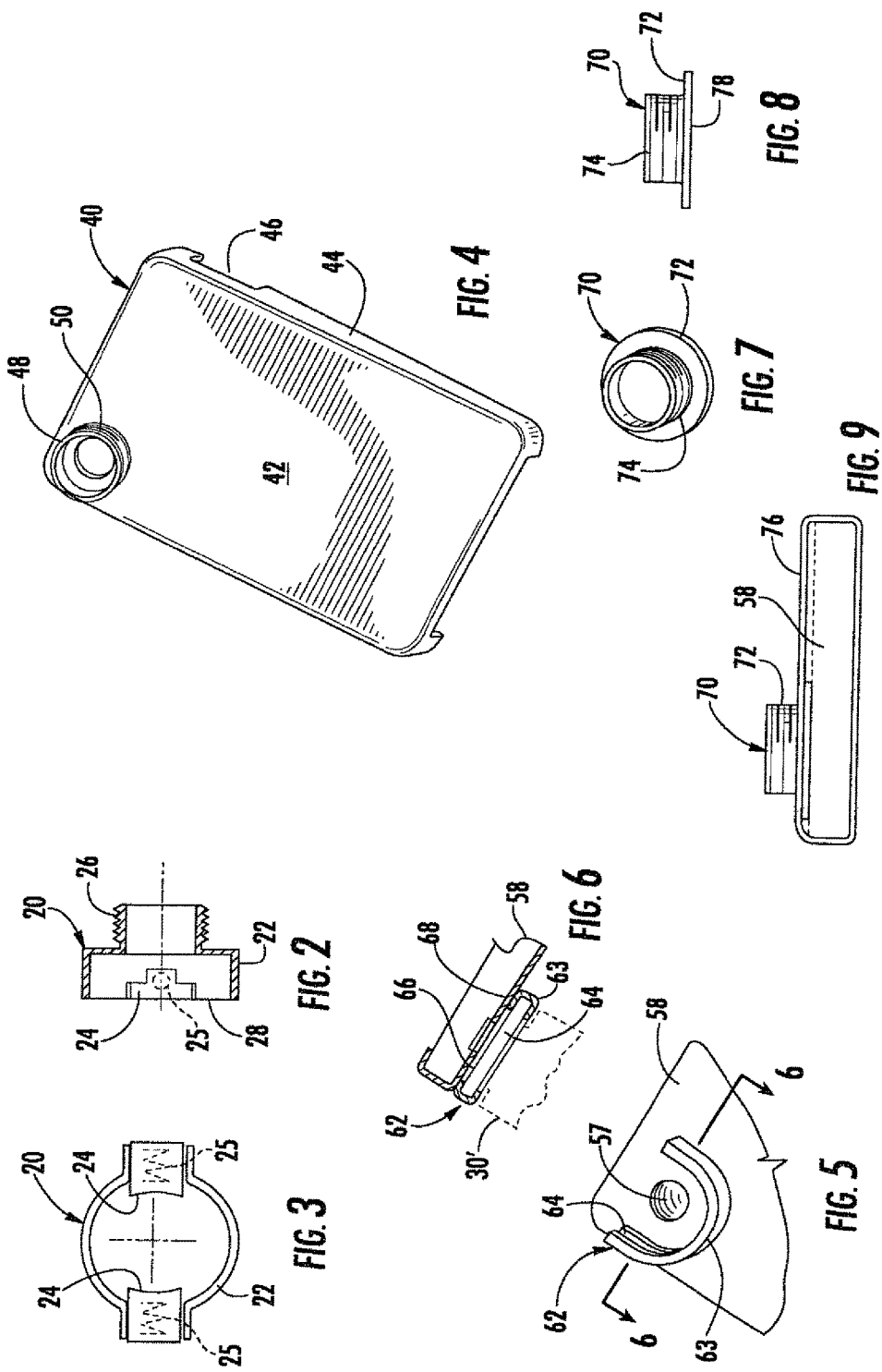

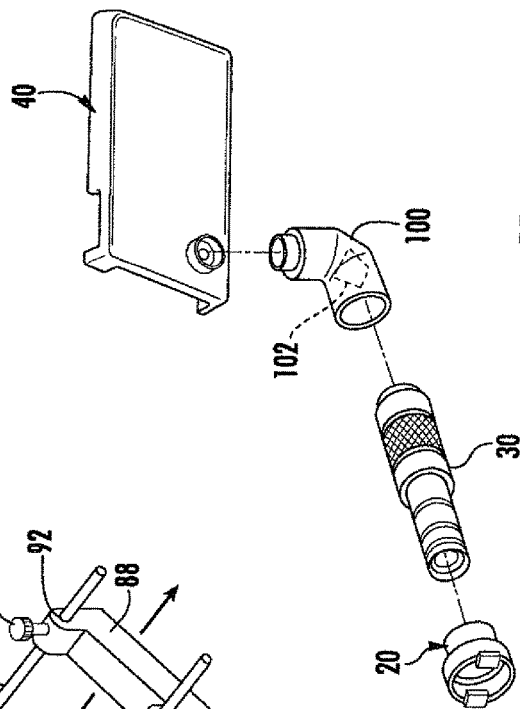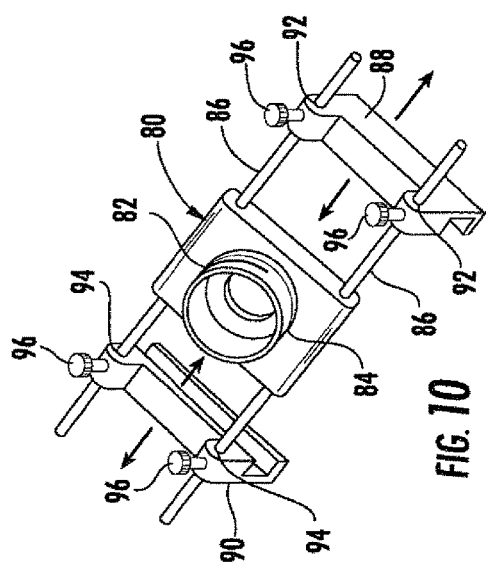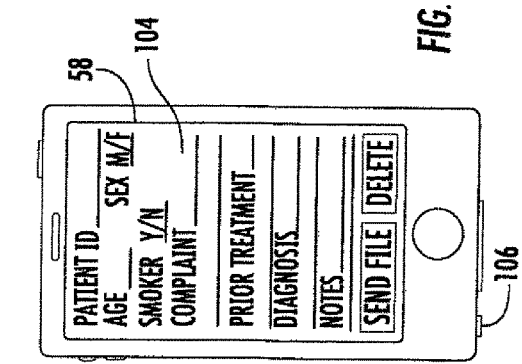

PED—ENDOSCOPE IMAGE AND DIAGNOSIS CAPTURE SYSTEM

PRIORITY CLAIM

This application is a continuation of PCT/US12/036573, filed May 4, 2012, and claims priority to U.S. Ser. No. 61/483,302, filed May 6, 2011. This application claims priority to all the applications and patents recited in this paragraph and all of the applications and patents recited in this paragraph are incorporated by reference in their entireties herein.

FIELD OF INVENTION

The invention relates to an adapter for a personal electronic device (PED), such as a smart phone or tablet PC, that allows it to be used to capture images and diagnostic data during an endoscopic examination, as well as a software program application (APP) for assisting with such use.

BACKGROUND

Endoscopes are used by medical professionals in a variety of situations. A fiberoptic flexible or rigid naso-pharyngo-scope (NPL scope) is used to examine the throat, larynx and sinuses of a patient in order to assist a physician in diagnosing and treating a patient's condition. Endoscopes are also used for GI and pulmonary examinations as well as various other uses. Laryngoscopes are used by anesthesiologists for the visualization of the larynx for intubation at the beginning of planned operations and during emergencies where the airway must be secured. They are also used by emergency medical responders for intubation of the airway in the field.

Currently, a video capture device can be connected to the fiberoptic endoscopes in order to display a video image on a separate display which can be seen by a doctor during an examination. This is typically used in endoscopic surgery procedures, and during some office examinations. However, in applications such as bedside or emergency room naso-pharyngo-laryngoscopy for examination of a patient's throat, it is both impractical and cumbersome, as well as very costly to use the known endoscopes which include a video camera connection. Further, since a physician requires two hands in order to insert a NPL scope, and the physician's attention is directed to the NPL scope as well as the patient in order to insert the scope, viewing a separate video display is impractical. Additionally, there are video display and capture devices used by anesthesiologists that are similarly expensive and cumbersome. Currently there are no ideal options for video capture of laryngoscopies by emergency medical responders for use outside of the hospital setting.

In teaching hospitals where resident physicians are required to consult with an attending senior physician to confer on a patient diagnosis, especially in otolaryngology, it is often necessary after the initial examination for the senior physician to re-insert the NPL scope for a further examination in order to confirm and/or discuss the initial diagnosis with the resident physician. This is inconvenient and uncomfortable for the patient, and can potentially delay medical decision making. Additionally, although relatively safe no exam is without potential adverse effects which become more likely with repeated exams. During the induction of anesthesia it is similarly important for a supervising physician to be able to observe the actions of the physician in training.

It would be desirable to provide an inexpensive and easily usable system for capturing endoscopic images during examination to allow for resident physicians to confer with senior physicians about diagnoses without further inconveniencing a patient. It would also be useful to have a catalogue of such images for diagnostic purposes. For office-based exams it would be beneficial to have an inexpensive method of recording and storing patient exams for longitudinal comparison, education of patients and their families, and sharing with consultants. For intubations both in and outside of the hospital it would be desirable to have a portable, inexpensive system for the display and capture of the laryngeal exam and intubation of patients.

SUMMARY

A personal electronic device (PED)-endoscope image and diagnosis capture system is provided. The system includes a PED adapter having a magnification lens connection side and a PED connection side. A magnification lens with a first end that is connectable with the lens connection side of the PED adapter is attached thereto. An eyepiece lens coupler with a magnification lens connection side and an endoscope eyepiece connection side is also provided. The magnification lens has a second end that is engagable with the eyepiece lens coupler and the endoscope eyepiece connection side is adapted to engage an endoscope eyepiece or a laryngoscope blade. A PED is connected to the PED adapter and includes a processor, a memory and an image capture system with a PED lens. The PED adapter aligns the magnification lens with the PED lens. The processor is configured to activate the image capture system using a remote or voice-activated trigger signal and store captured images in the PED memory, or is activated for video and audio recording the beginning of the exam and captures the entire exam. Preferably, the PED adapter when not coupled to the magnification piece acts as a protective cover for the PED. It can remain attached to the PED even when not being used with the magnification piece for expedient attachment when needed.

In another aspect, the invention provides a PED with a software program application (APP) configured for capturing an endoscopic image and diagnostic data. The PED has a processor, a memory and an image capture system with a PED lens. The PED lens is adapted to be connected to an endoscope by a magnifying lens. The processor is configured via the APP to activate the audio and/or image capture system upon being triggered by a user, to store captured image and/or audio in memory, to display a patient examination and diagnosis input screen for receiving patient data input by the user and associating the patient data with the captured image, and to transmit the captured image and/or audio and the patient data wirelessly to an external system. Preferably, the external system is an electronic medical records system and data is transmitted using the PED wireless transmission features.

In another aspect, an adapter for coupling a personal electronic device having an image capture system to an endoscope is provided. The adapter includes a PED adapter having a magnification lens connection side and a PED connection side. A magnification lens with a first end is connected with the lens connection side of the PED adapter. An eyepiece lens coupler with a magnification lens connection side and an endoscope eyepiece connection side is provided, and the magnification lens has a second end that is engagable with the eyepiece lens coupler. The endoscope eyepiece connection side is adapted to engage an endoscope eyepiece or laryngoscope.

The PED adapter preferably includes three separate functional units that are interchangeable and independent from the adjacent unit. The eyepiece lens coupler provides a removable attachment to the endoscope or laryngoscope and/includes a simple clasp that acts as a universal adapter to known endoscope eyepieces or laryngoscope blades. The magnification lens is preferably a series of lenses in a housing that includes at least a focusing adjustment. A zoom adjustment can also be provided, if desired. Preferably, the magnification is in the range of 4×-8× and more preferably 6× magnification. Higher magnification can be included for endoscopic microscopy. An angle adjustment can also be provided to allow for use with both flexible and rigid endoscopes. The PED adapter can be formed as a PED case having a lens adapter affixed thereto, with the case being of the known type of smart phone or PED cases that are commonly available. The lens adapter is affixed to or molded on the case and allows for convenient connection and removal of the magnification lens. Alternatively, an adapter can be provided which is adhered directly onto the PED case that is non-intrusive and therefore can remain in place even when the magnification lens is not attached. It is also possible to provide a universal adapter, in the form of a strap-on adapter or an adapter with adjustable side walls which can be adjusted to conform to the dimensions of any PED.

Alternatively the lens adapter would be attached to a blade similar to ones used by anesthesiologists for direct laryngoscopy for intubation. This blade would be made of plastic, metal, or similar material; have a curvature and shape similar to commonly used Miller or Macintosh laryngoscope blades, a light source and fiberoptic cable allowing for alignment of the fiberoptic cable with the magnification lens. The PED would record and display the images seen by the laryngoscope during laryngoscopy for intubation. Alternatively a magnification component and coupling component would be able to attach to currently used blade and light source/handle configurations to provide images and recording of the laryngoscopy on a PED.

The APP for the PED preferably includes additional functionality such as allowing for an audio input to be stored along with the image in the PED memory. Further, the APP preferably allows the processor to create and display data input fields on a display screen of the PED allowing for input of data relating to at least one of a patient identification, age, sex, smoking status, complaint, pre/post-op, previous treatment, diagnosis, location of lesion, or other user observations or data. Further, the APP preferably directs the processor to create and display prompts on the display screen for transfer of the captured image to a separate data collection and storage system such as an electronic medical records system that stores patient records and data. The APP can also include an approval screen for patient consent that can be signed or keyed by the patient. Additional features allowing for audio and video editing and dubbing can also be provided by the APP.

BRIEF DESCRIPTION OF THE DRAWINGS

The foregoing summary as well as the following detailed description will be better understood when read in conjunction with the appended drawings. In the drawings:

FIG. 2 is a cross-sectional view through an eyepiece lens coupler.

FIG. 3 is an end view of the eyepiece end coupler of FIG. 2.

FIG. 4 is a perspective view of a PED case with a lens adapter connected thereto.

FIG. 5 is a perspective view of a portion of a PED with an alternate embodiment of a PED adapter affixed thereto.

FIG. 6 is a cross-sectional view taken along line 6-6 of FIG. 5.

FIG. 7 is a perspective view of a second alternate embodiment of a PED adapter that can be used with any type of PED.

FIG. 8 is an elevational view of the PED adapter of FIG. 7.

FIG. 9 is an end view showing the PED adapter of FIGS. 7 and 8 connected to a PED.

FIG. 10 is a perspective view of a universally adjustably PED adapter.

FIG. 11 is a perspective view showing an angle adapter connected between the PED adapter and the magnification lens.

FIG. 12 is a view of a PED display screen showing examples of patient data and diagnosis input fields.

DETAILED DESCRIPTION OF THE PREFERRED EMBODIMENTS

Figure 1:
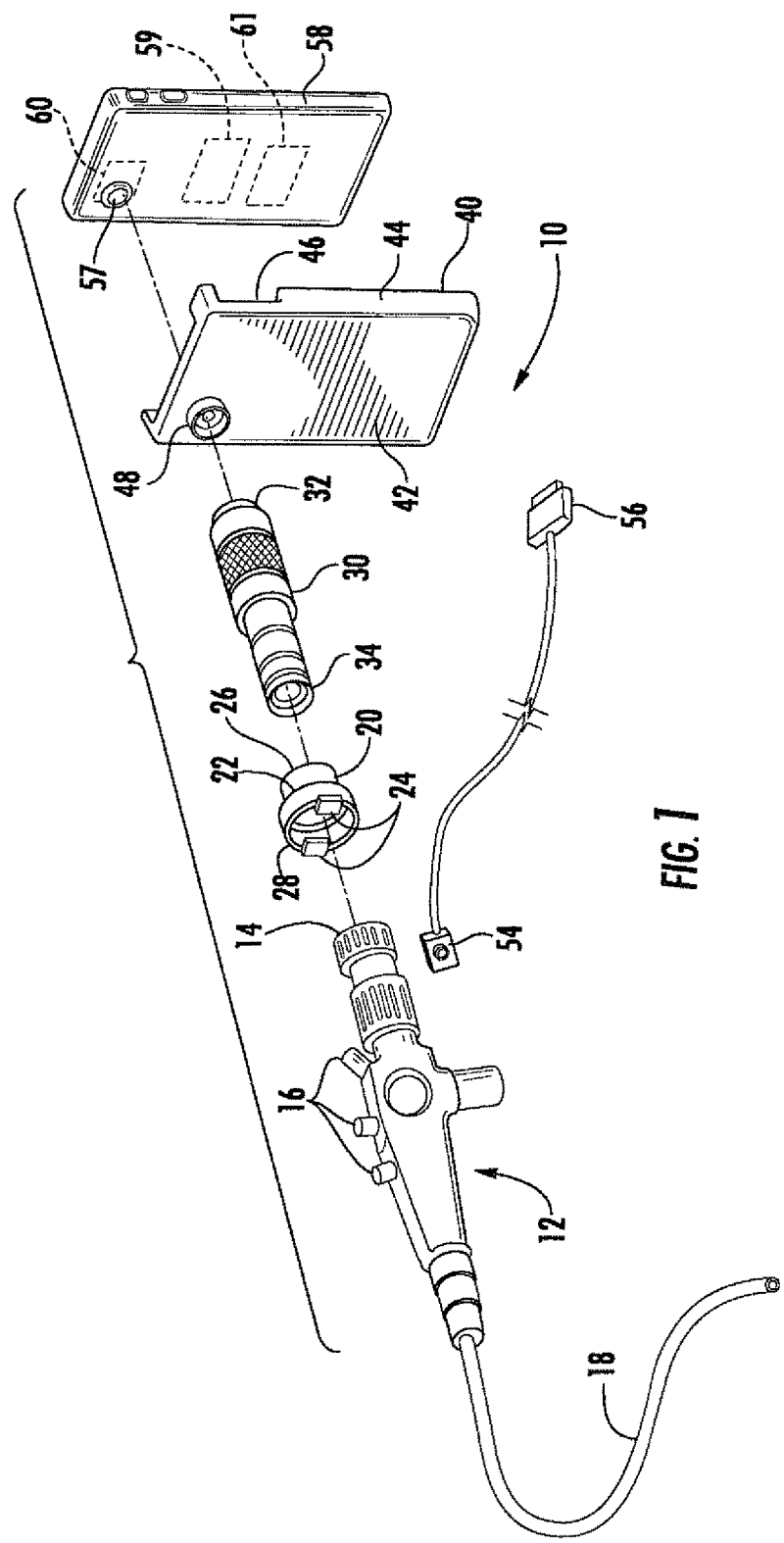
FIG. 1 is an exploded perspective view of the PED-Endoscope Image and Diagnosis Capture System according to the invention.

Certain terminology is used in the following description for convenience only and is not considered limiting. Words such as "front", "back", "top," and "bottom" designate directions in the drawings to which reference is made. This terminology includes the words specifically noted above, derivatives thereof and words of similar import. Additionally, the terms "a" and "one" are defined as including one or more of the referenced item unless specifically noted. A "PED" is any type of personal electronic device that includes an image capture system and wireless communication capabilities, and can be for example, smart phones such as the I-Phone™ or Android™ phone, a tablet PC or other suitably equipped devices. As used herein "endoscope" is intended to refer generically to any type of endoscope, laryngoscope, GlideScope or other medical scope that is inserted into a patient to carry out an examination or procedure.

The preferred embodiments of the present invention will be described with reference to the drawings where like numerals represent like elements throughout, Referring to FIG. 1, a personal electronic device (PED)-Endoscope Image and Diagnosis Capture System 10 (hereafter "system 10") is shown. Here the components are separated from one another in order to provide a clear illustration. The system 10 is adapted for use in connection with an endoscope 12 which can be an otolaryngoscope or any other type of endoscope. Such endoscopes typically include an eyepiece 14 as well as ports 16 for insertion of air, fluids or a flexible catheter. The tip of the endoscope 12 illustrated is a flexible tip 18. However, it can be a rigid or semi-rigid tip, depending upon the particular application.

The system 10 includes an eyepiece lens coupler 20, which is shown in further detail in FIGS. 2 and 3. The eyepiece lens coupler 20 preferably includes a body 22 having engaging members 24 which are biased via springs 25 into a position whereby they would become engaged behind the eyepiece 14 of the endoscope 12, upon installation. The eyepiece lens coupler 20 includes a first, coupling end 26, preferably with threads, that is adapted to engage a magnification or zoom lens 30, described in further detail below. The second end 28 of the eyepiece lens coupler includes the engaging members 24 which are adapted to engage the eyepiece 14 of the endoscope 12.

In the preferred embodiment, the lens coupler 20 can be formed of a metal or polymeric material. Lenses can be provided to adjust to the focal length to the endoscope eyepiece. Various couplers are known for attaching cameras to eyepieces, such as the C-mount Adaptor from Lighthouse Imaging Corp., Portland, Me., and accordingly, various configurations on the second end 28 could be provided that are different from the engaging members 24 illustrated.

Referring again to FIG. 1, a magnification lens 30 is provided. The lens is preferably of the known type and has a magnification of 4× to 8×, and most preferably 6× magnification. The magnification lens can also be a zoom lens, preferably with the magnification is in the range of at least 2× to 8×. Higher magnification can be provided to allow for endoscopic microscopy.

As such magnification lenses are known, a further description is not provided here. However, the first end 32 and the second end 34 are configured with connector elements, which can be various types of connectors such as a threaded end for a threaded connection or an annular groove for engagement by a coupling or clip. Preferably, the magnification lens 30 includes a separate focus adjustment which can be adjusted by a user.

Referring to FIGS. 1 and 4, the system 10 further includes a PED adapter, which in the first embodiment comprises a PED case 40. The PED case 40 has a base 42 with side walls 44 which are adapted to allow the case 40 to be attached to a PED, such as a smart phone or other device having wireless communication capability as well as an image capture system. The case 40 preferably has cutouts 46 located at the control buttons as well as any microphone for audio input. A lens adapter 48 is connected to the base 42 in a position that is adapted to be aligned with the PED lens 57 of the PED 58. The lens adapter 48 may include threads, as shown in FIG. 4, or it can provide for a snap or other type of connection to the magnification lens 30.

Still with reference to FIG. 1, an exemplary PED 58 is shown. The PED 58 includes a processor 59 as well as an image capture system 60 preferably in optical communication with the PED lens 57. The processor 59 is in communication with a memory 61. The PED also includes a PED display 104, shown in FIG. 12, as well as a microphone or other audio input 106. Such PED's 58 can be any type of smart phone, such as an I-phone™, ANDROID™ phone or any other personal electronic device that includes image capture and wireless communication capabilities along with the ability for the processor 59 to be programmed to perform specific functions.

Still with reference to FIG. 1, an on/off push-button switch 54 with a plug 56 that can be plugged into the PED 58 is optionally provided. Optionally, multiple buttons to control image/video capture and audio capture can be included. The on/off push-button switch 54 can be used to control the image capture function of the PED 58. Preferably, the cord is sufficiently long so that the push-button switch 54 can be positioned on the endoscope 12 for ease of use. The button housing preferably includes an adjustable attachment for securing the button housing to the scope in various configurations. Alternatively, as described in more detail below, the APP for the PED 58 can provide for voice-activated control.

Referring to FIGS. 5 and 6, a second embodiment of a PED adapter 62 is shown. The PED adapter 62 has a C-shaped body 63 with a groove 64 defined in the internal portion of the C. An adhesive layer 68 is attached to the base 66 of the C-shaped body 63 which allows the PED adapter 62 to be adhered directly to the housing of the PED 58. As shown in FIG. 6, the magnification lens 30' includes a groove which corresponds to the C-shaped body 63 allowing the magnification lens 30' to be slid into position in the C-shaped body 63. Here, the PED adapter 62 would remain on the PED housing when the system 10 is not in use with the magnification lens 30' being disconnected.

Referring to FIG. 9, a third embodiment of the PED adapter 70 is shown. Here the PED adapter 70 includes a base 72 connected to a threaded ring 74, as shown in FIG. 7. This can be attached to the PED 58 using a strap 76, as shown in FIG. 9. Alternatively, an adhesive layer 78 can be applied to the base 72 for installation in a similar manner to the PED adapter 62. It would also be possible to provide a magnet on the base 72 and to adhere a ferrous ring to the housing to allow for a magnetic coupling. However here, the threaded rings 74 is adapted to be attached to a threaded first end 32 of the magnification lens 30.

Referring to FIG. 10, a universal PED adapter 80 is shown. The universal adapter 80 includes a lens connector body 82 with a threaded ring 84 located thereon. Rods 86 extend from the lens connector body 82. Adjustable side walls 88, 90 having openings 92, 94, respectively, are slidably located on the rods 86. The adjustable side walls 88, 90 can be slid on the rods 86 in order to position the threaded ring 84 in position over the PED lens 57 in order to properly align the magnification lens 30 with the PED lens 57. The adjustable side walls 88, 90, which can be slid up and down the sides of the PED 58 in a direction transverse to the rods 86, are then affixed in position using the screw clamps 96. It would also be possible to have the connector body 82 slidable on the rods 86 for fine tuning the position, and lock the connector body 86 in place with at least one screw clamp 96.

Figure 19:
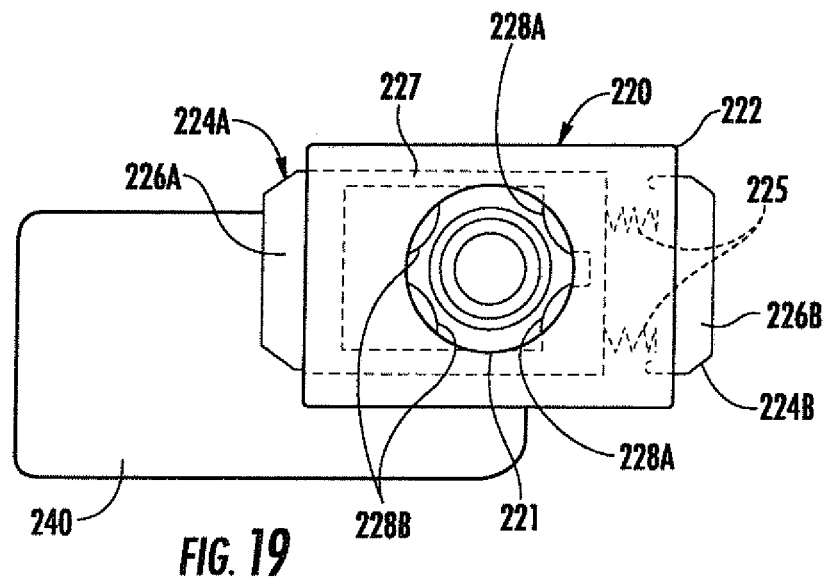
FIG. 19 is a top plan view of another embodiment of a PED case with a lens adapter, lens, and eyepiece lens coupler connected thereto.
Figure 20:
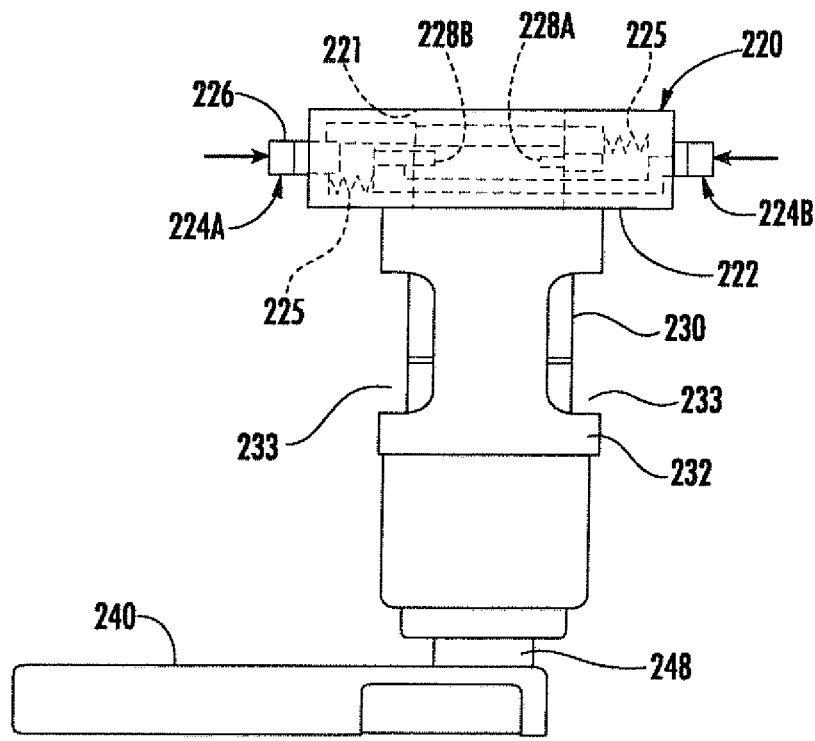
FIG. 20 is a side elevational view of the PED case with lens adapter, lens, and eyepiece lens coupler shown in FIG. 19.

Referring to FIGS. 19 and 20, another embodiment of a PED case 240 with a lens adapter 248, magnification lens 230, and eyepiece lens coupler 220 is shown for use in connection with the system 10. This embodiment is similar to the embodiment of FIG. 1, and the case 240, lens adapter 248 and magnification lens 230 are similar or the same as the corresponding parts described above in connection with the embodiment of FIG. 1. Here, the eyepiece lens coupler 220 is designed to provide a more stable connection to the magnification lens 230 as well as to the eyepiece of the endoscope. This is achieved by providing the coupler body 222 of the eyepiece lens coupler 220 with a tubular extension 232 that engages around the lens 230, with cutouts 233 provided in the tubular extension 232 for adjusting the magnification and/or focus of the lens 230. The tubular extension 232 extends from the coupler body 222, preferably in one piece, and can be clamped or otherwise connected to the lens 230.

As shown in FIGS. 19 and 20, the coupler body 222 holds two opposing engaging members 224A, 224B that are adapted to slide inwardly by pressing the actuating ends 226A, 226B toward one another. FIG. 19 shows the engaging member 224A in detail with broken lines within the coupling body 222, which is hollow in order to hold the engaging members 224A, B in a slidable manner. The engaging member 224A includes two side rails 227 that extend from the actuating end 226A toward the opposite side. At least one, and preferably two, engaging tabs 228 are connected to the side rails 227. At least one spring 225 biases the engaging member 224A into a position where the engaging tabs are adapted to engage behind an eyepiece of the endoscope. As shown in FIG. 20, the engaging member 224B has the same construction, but extends in the opposite direction. The engaging tabs 228A, B extend inside a periphery of the eyepiece receiving opening 221 in the body 222. In use, the user squeezes the two actuating ends 226A, B together against the force of the springs 225 so that the engaging tabs 228A, B are pressed into the hollow body and out of the area defined by the opening 221, so that the eyepiece of the endoscope can be received therein. The actuating ends 226A, B are then released, and the springs 225 force the engaging members back to the position shown in FIG. 19, so that the engaging tabs 228A, B are engaged behind the endoscope eyepiece.

Preferably, the body 222 and the tubular extension 232 are made of a polymeric material or of a surgical grade steel. The engaging members 224A, B can also be made of the same materials. The body 222 can have a removable cover in order to allow assembly of the engaging members 224A, B and springs 225 in the hollow interior. Suitable guides for guiding the sliding movement of the engaging members 224A, B in the body 222 are preferably also formed or located therein.

For each of the PED adapters, the components can be formed of polymeric or metallic materials, depending upon the particular application. With respect to the PED case 40, 240, this can be made in various configurations and sizes to fit any of the various commercially available PED's 58. The PED case 40, 240 can be used in place of a generic PED case with the magnification lens 30, 230 and eyepiece lens coupler 20, 220 only being attached as needed. With respect to the alternative embodiments, these are intended to be used with any PED 58 and therefore avoid the need for a specific case for each of the various types of PED's 58 that are available.

Referring to FIG. 11, it is also possible to provide an angle adapter 100 having an internal prism 102 or reflective surface (not illustrated) located therein in order to change the viewing angle of the PED 58. The angle adapter 100 is preferably located between the PED adapter 40 and the magnification lens 30. While a prism 102 is shown, those skilled in the art will recognize that other types of angled optical connectors can be utilized as the angle adapter 100. It would also be possible to provide a flexible coupling to adjust the angle using a coherent fiber optic bundle.

According to the invention, it is also provided that a light source can be integrated into the eyepiece lens coupler or the lens adapter. This can be battery powered and provided with an on-off switch and LEDs as the light emitting element. A light guide connects the emitted light to the scope or allows the light to travel along the optic path through the eyepiece lens coupler via a prism. Alternatively, the case 240 can include a light guide, such as an optic fiber bundle, that is aligned with a light source on the PED that provides light to a port on the scope that is adapted to be attached to a light source.

Referring now to FIGS. 13-16, the functionality and use of the system 10 as well as the APP for the PED 58 which forms part of the system 10 will be described in detail. As shown in Box 112, a user would first attach the magnification lens 30 to the PED 58 and to the endoscope eyepiece 14 using the PED adapter 40, 62, 70, 80 and eyepiece lens coupler 20, described above. The push-button on/off switch 54 is optionally connected to the PED 58 using the plug 56, as indicated at Box 114. As shown in Box 116, the user would then select the endoscope APP so that it runs on the processor 59 in the PED 58. This is preferably done through a graphical user interface on the display 104, which can be a touch screen or cursor driven selection on the display. By running the APP, the processor 59 is configured to activate the image capture system 60 using a remote or voice activated trigger signal in order to store captured images in the PED memory 61. The user then inserts the endoscope and guides the tip to the site to be examined, as indicated in Box 120. Here, the user activates the on/off push button switch 54 or uses voice activation for capturing still or video images of the site, as indicated at Box 122. The images are stored as image data in the PED memory 61. As indicated in Box 124, optionally, the processor 59 is configured by the APP to capture audio data in connection with the activation of the image capture system and stores the audio data in the PED memory 61.

As shown in Box 126, the user can then enter data related to at least one of a patient identification, age, sex, smoking status, complaint, pre/post-op, previous treatment, diagnosis, location of lesion, or other user observations. These are preferably input into fields on the display 104 generated by the processor 59, for example as shown in FIG. 12. The user is then able to use the PED 59 to send the image, audio and patient related data to an electronic medical records system, as indicated in Box 128.

Preferably, the APP is HIPPA compliant and uses the required passwords and encoding required to protect patient data and maintain confidentiality. Alternatively, the data can be exported on a flash drive, hard drive or disc connected to the PED 58.

Figure 13:
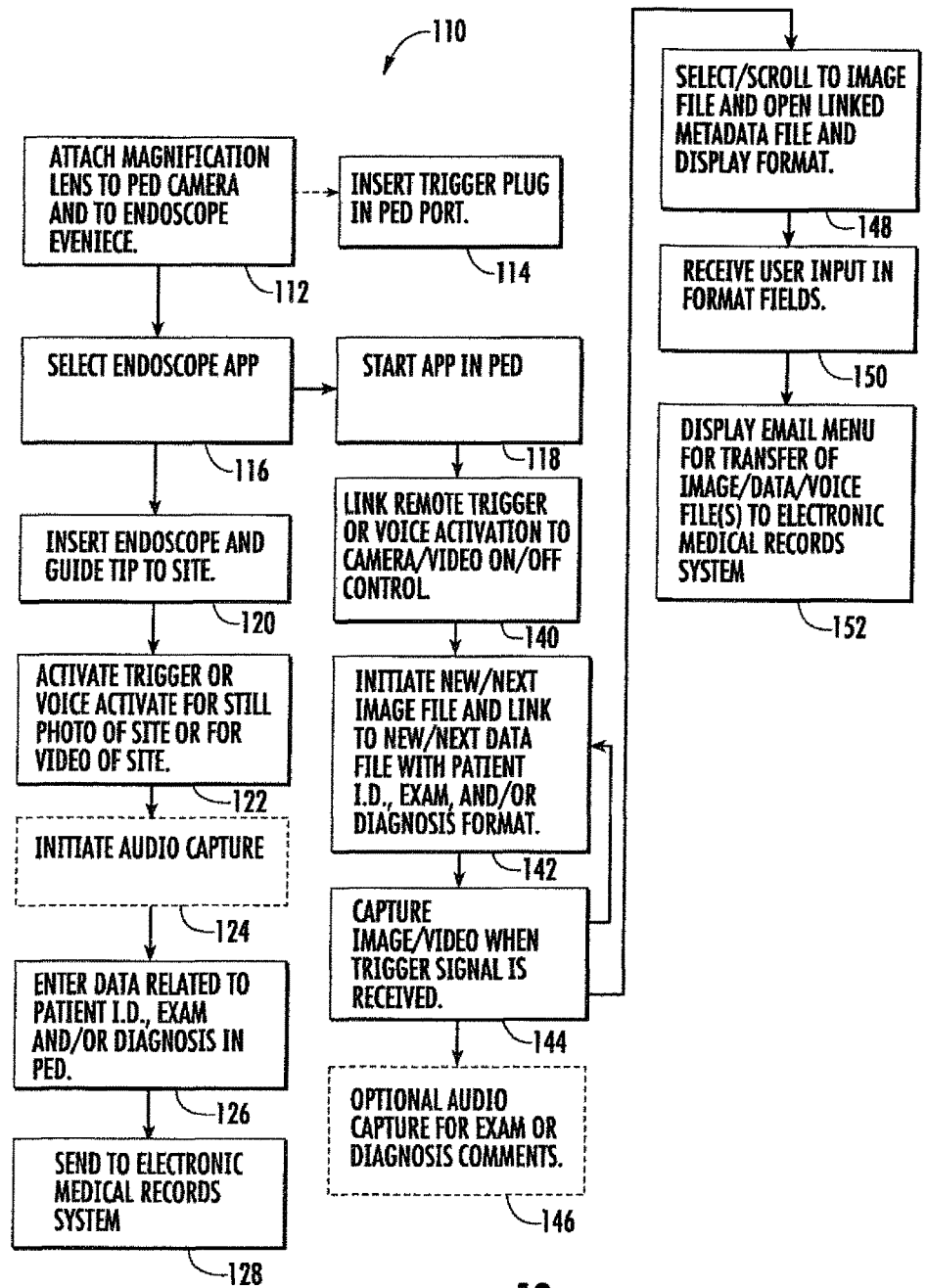
FIG. 13 is a flow chart showing the operation of the PED. Endoscope Image and Diagnosis Capture System and the APP functionality.

Still with reference to FIG. 13, the APP that is loaded into the processor 59 of the PED 58 is described in further detail. When the APP is started in the PED, as indicated in Box 118, the processor 59 links the remote on/off switch 54 or voice activation to the camera/video on/off controls resident in the PED 58, as indicated at Box 140. As indicated in Box 142, upon activation of the camera/video on/off control, the APP configures the processor 59 to initiate a new or next image file and links the new or next image file to a new or next data file where the patient ID and patient data can be input, for example as shown in FIG. 12. The APP configures the processor 59 to capture the image/video when the trigger signal is received as indicated in Box 144 and optionally configures the processor 59 to store audio data relating to the examination or diagnosis that is made during insertion of the endoscope and/or capture of the image or video as shown in Box 146. To the extent that multiple still images are required, the steps in Boxes 142 and 144 are repeated. Once the image and/or video and/or audio signals are captured, the APP configures the processor 59 to open a linked metadata file and display the input format, such as shown in FIG. 12 for patient ID as well as other data, as noted above, with respect to the patient status, issue, diagnosis as well as other observations. As indicated in Box 150, the processor is configured to receive user inputs in these formatted fields through the PED 58 data entry system, which can be an onscreen keyboard or a separate keyboard provided on the PED 58.

The processor 59 is further configured by the APP to display an e-mail or other data transfer menu for transfer of the image/data/voice files to an electronic medical records system, as shown in Box 152.

Figure 14:
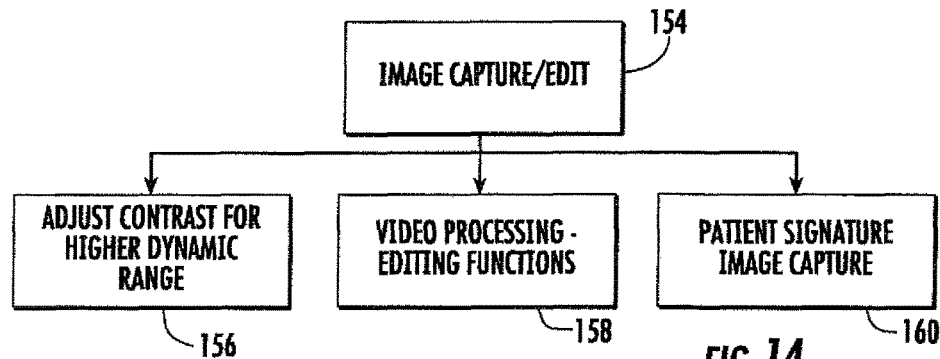
FIG. 14 is a flow chart showing the image capture and edit functionality of the APP.

Additional functionality can be provided by the APP program loaded in the processor 59. As shown in FIG. 14, preferably an image capture and editing process is provided as indicated in Box 154. As shown in Box 156, preferably controls are provided to adjust the contrast for higher dynamic range in order to enhance certain visual features being observed. As shown in Box 158, video processing and editing functions can be also be provided to edit the video that is captured. These functions would be similar to the functionality provided for video editing which are known to those skilled in the art. Further, the APP can configure the processor 59 to display a patient signature image capture for any required releases or acceptance for treatment which can then be linked with the image/data/voice files created for the examination and transferred to the electronic medical records system with the other data from the examination.

Figure 15:
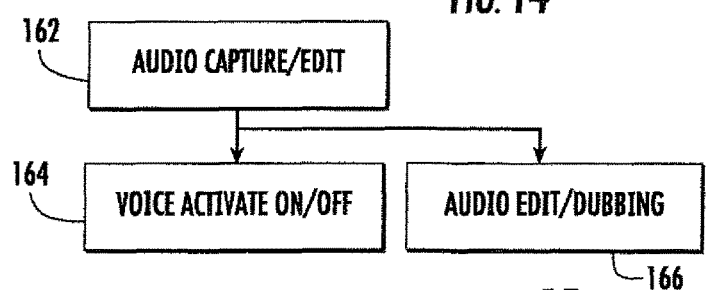
FIG. 15 is a flow chart showing the audio capture and edit functionality of the APP.

Referring to FIG. 15, it is also possible to provide an audio capture and editing system as indicated in Box 162. This would preferably include voice activation as indicated in Box 164 for turning on and off the audio pickup. Further, audio editing and dubbing functions can be provided by the APP and loaded in the processor 59 as indicated in Box 166.

Figure 16:
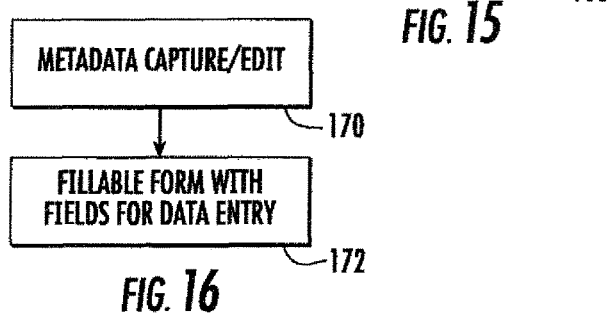
FIG. 16 is a flow chart showing the metadata capture and edit functions of the APP.

Referring to FIG. 16, in connection with the user inputs in the format fields for patient related data, preferably a metadata capture and editing function is provided as indicated in Box 170. This allows a user to not only fill the forms but also to later edit the filled in data as indicated in Box 172.

Figure 17:
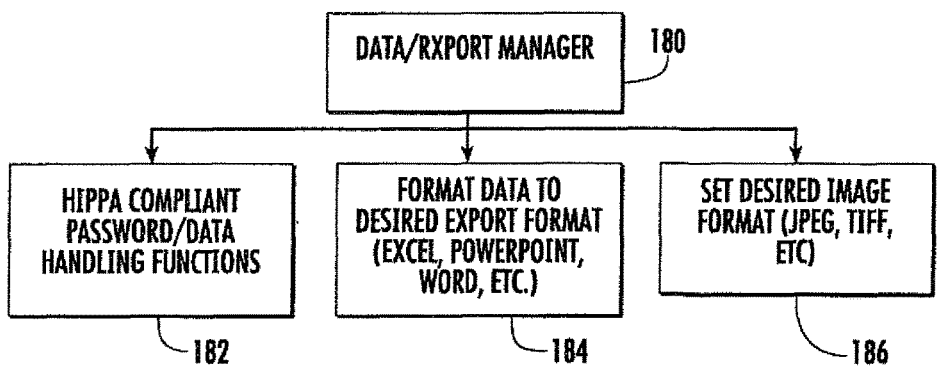
FIG. 17 is a flow chart showing the data export managing functions of the APP.

Referring to FIG. 17, additionally, the APP includes software that configures the processor 58 to provide data export managing functions as indicated in Box 180. This includes the HIPPA compliant password and data handling functions as indicated in Box 182. Further, as indicated in Box 184, the data can be formatted to a desired export format, such as Excel, PowerPoint, WORD, etc. Further, the image format can be set to a desired file type, such a jpeg, tiff, etc., as indicated in Box 186.

Figure 18:
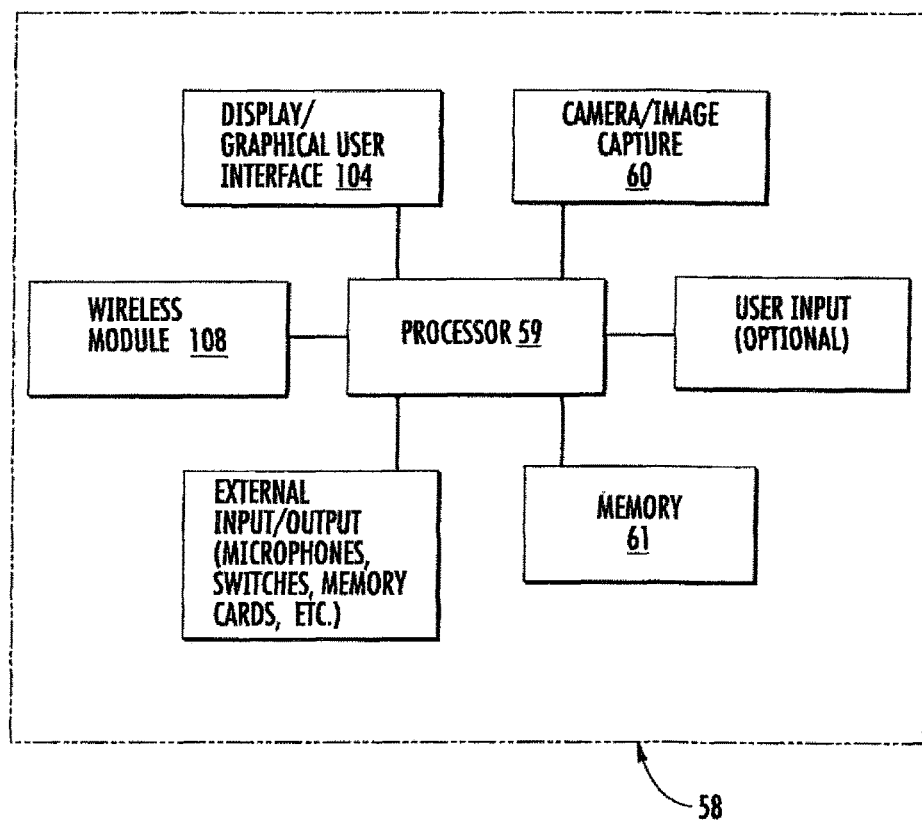
FIG. 18 is a schematic diagram of the PED functional elements.

Finally, referring to FIG. 18, the functional units associated with the PED 58 are shown in a schematic functional diagram with the various functional elements that communicate with the processor 59.

The system 10 according to the invention provides an inexpensive and easy to use endoscope image and diagnosis capture ability that is currently unavailable. This can be used by trainees and experienced physicians in order to share data, confer on diagnoses with remotely located physicians, as well as to create a record of the examination which can be further reviewed. This uses the ability that is resident in a variety of PED's that are already used or are available to physicians with known endoscopes which are already in the medical facility to create an improved functionality to enhance medical care while maintaining lower cost. Further, it allows for automated updating of the patient's electronic medical records, consent form as well as various other types of documentation for patient consent. Further, for patients with a changing medical status, the invention allows providers to easily record the laryngeal, pharyngeal or other endoscopic findings and to monitor changes, which can make a substantial difference in patient care as conditions change. Additionally, other adaptations could include a similar arrangement with attachment of the lens assembly to intubating laryngoscopes, otoscopes, operative microscopes, etc.

Those skilled in the art will recognize that some or all of the above-noted features of the invention can be used alone or in various combinations in order to provide the desired level of functionality for the device and system according to the invention. Accordingly, the invention is not limited to the preferred embodiments described, and is intended to cover devices and systems that come within the scope and spirit of the invention as defined by the appended claims.

The invention claimed is:

1. A personal electronic device (PED)-endoscope image and diagnosis capture system, comprising:
    a PED adapter that is a cell phone case having a magnification lens connection side, a PED connection side and an opening;
    a lens adapter molded to the PED adapter;
    a magnification lens having a first end that is connectable with the magnification lens connection side of the PED adapter through the lens adapter, and a second end;
    an eyepiece lens coupler with a magnification lens connection side that is adapted to engage with the second end of the magnification lens and an endoscope eyepiece connection side that comprises at least two engaging tabs that are configured to engage behind an endoscope eyepiece, wherein the engaging tabs are further configured to secure a connection of the endoscope eyepiece to the eyepiece coupler;
    a PED connected to the PED adapter and having a processor, a memory and an image capture system with a PED lens, where the PED lens is aligned with the opening of the PED adapter and the magnification lens; and
    wherein the processor is configured to activate the image capture system using a remote or voice-activated trigger signal and store captured images in the PED memory.

2. The PED-endoscope image and diagnosis capture system of claim 1, wherein the PED has an audio input and the processor is configured to capture audio data in connection with activation of the image capture system and store the audio data in the PED memory.

3. The PED-endoscope image and diagnosis capture system of claim 1, wherein the processor is configured to create and display data input fields on a display screen of the PED including fields for input of data relating to at least one of a patient identification, age, sex, smoking status, complaint, pre/post-op, previous treatment, diagnosis, location of lesion, or user observations.

4. The PED-endoscope image and diagnosis capture system of claim 1, wherein the processor is configured to activate the image capture system for still photos or a video image.

5. The PED-endoscope image and diagnosis capture system of claim 1, wherein the processor is configured to create and display prompts on a display screen of the PED for transfer of the captured images to a separate data collection and storage system.

6. The PED-endoscope image and diagnosis capture system of claim 1, wherein the processor is configured to create and display a patient consent form on a display screen of the PED.

7. The PED-endoscope image and diagnosis capture system of claim 1, wherein the magnification lens provides a magnification of 4× to 8×.

8. The PED-endoscope image and diagnosis capture system of claim 1, further comprising an image capture trigger switch having a plug that is connected with an input plug of the PED and communicates with the processor.

9. A personal electronic device (PED) configured for capturing endoscopic image and diagnostic data, comprising:
a processor, a memory and an image capture system with a PED lens, the PED lens being adapted to be connected to an eyepiece of an endoscope via a PED adapter, a lens adapter, a magnifying lens and an eyepiece lens coupler that comprises at least two engaging tabs that are configured to engage behind the endoscope eyepiece, wherein the lens adapter is molded to the PED adapter; the processor being configured to activate the image capture system using a remote or voice-activated trigger signal for capturing a still or video image, to store a captured image in memory, to display a patient exam and diagnosis input screen for receiving patient data input by the user and associating the patient data with the captured image, and to transmit the captured image and the patient data wirelessly to an external system.

10. The PED of claim 9, wherein the processor is further configured to activate the image capture system to capture video images.

11. The PED of claim 9, wherein the processor is further configured to allow a user to edit the captured images.

12. The PED of claim 9, wherein the processor is further configured to activate an audio input and capture audio data and associate the audio data with the captured image.

13. The PED of claim 12, wherein the processor is further configured to allow a user to edit the captured audio data.

14. The PED of claim 9, wherein the processor is configured to provide HIPPA compliant password and data handling functions.

15. An adapter for coupling a personal electronic device (PED) with an image capture system to an endoscope, comprising:
a PED adapter that is a cell phone case having a magnification lens connection side, a PED connection side and an opening;
a lens adapter molded to the PED adapter;
a magnification lens having a first end that is connectable with the magnification lens connection side of the PED adapter through the lens adapter and is aligned with the opening of the PED adapter, and a second end; and
an eyepiece lens coupler with a magnification lens connection side that is adapted to engage with the second end of the magnification lens and an endoscope eyepiece connection side that comprises at least two engaging tabs that are configured to engage behind an endoscope eyepiece, wherein the engaging tabs are further configured to secure a connection of the endoscope eyepiece to the eyepiece coupler.

16. The adapter of claim 15, further comprising an angle adapter located between the magnification lens connection side of the PED adapter and the magnification lens.

\* \* \* \* \*